US008920482B2

(12) United States Patent
McHugo (10) Patent No.: US 8,920,482 B2
(45) Date of Patent: Dec. 30, 2014

(54) STENT DELIVERY SYSTEM

(75) Inventor: Vincent McHugo, Birdhill (IE)

(73) Assignee: Cook Medical Technologies LLC, Bloomington, IN (US)

( * ) Notice: Subject to any disclaimer, the term of this patent is extended or adjusted under 35 U.S.C. 154(b) by 190 days.

(21) Appl. No.: 13/534,602

(22) Filed: Jun. 27, 2012

(65) Prior Publication Data

US 2013/0006347 A1    Jan. 3, 2013

Related U.S. Application Data

(60) Provisional application No. 61/503,231, filed on Jun. 30, 2011.

(51) Int. Cl.
*A61F 2/06* (2013.01)
*A61F 2/95* (2013.01)

(52) U.S. Cl.
CPC ........... *A61F 2/95* (2013.01); *A61F 2002/9511* (2013.01)
USPC .......................................... 623/1.11; 606/108

(58) Field of Classification Search
CPC ........................... A61F 2/95; A61F 2002/9511
USPC ........................ 606/108; 623/1.11, 1.12, 1.23
See application file for complete search history.

(56) References Cited

U.S. PATENT DOCUMENTS

| 4,913,141 | A | 4/1990 | Hillstead |
| 8,128,680 | B2 * | 3/2012 | Arnault De La Menardiere et al. ............................ 623/1.23 |
| 2005/0288764 | A1 | 12/2005 | Snow et al. |
| 2009/0030497 | A1 | 1/2009 | Metcalf et al. |
| 2009/0204202 | A1 | 8/2009 | Dierking et al. |

* cited by examiner

*Primary Examiner* — Victor Nguyen
(74) *Attorney, Agent, or Firm* — Brinks Gilson & Lione (57) ABSTRACT

A stent delivery system and method are provided. The system includes an inner elongate shaft and an outer elongate shaft, the inner elongate shaft coaxially extends at least partially within the lumen of the outer elongate shaft and the inner and outer elongate shafts are movably positionable relative to each other. The system also includes a stent positionable on the inner elongate shaft, the stent having a plurality of openings and a restraining wire where a proximal portion is operably connected to one of the inner and the outer elongate shaft and the distal portion is operably connected to the other of the inner and the outer elongate shaft. Movement of the inner and outer elongate shafts relative to each other in a first direction applies tension to at least a portion of the restraining wire to move the stent to the collapsed configuration.

16 Claims, 7 Drawing Sheets

STENT DELIVERY SYSTEM

RELATED APPLICATIONS

This application claims the benefit of U.S. Provisional Application No. 61/503,231, filed Jun. 30, 2011, which is incorporated by reference herein in its entirety.

TECHNICAL FIELD

This invention relates to a medical device and, in particular to a device for delivering and deploying a self-expanding stent and a method of delivering and deploying the stent into a body lumen.

BACKGROUND

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling back the outer sheath relative to the inner catheter until the stent is exposed. The self-expanding stent expands from the stent distal end to the stent proximal end as the sheath is proximally withdrawn.

Several problems may occur with the sheathed delivery device described above. The sheath release delivery devices are difficult to reposition or remove and slow to operate. The stent may only be partially deployed prior to reconstrainment of the stent by the sheath in order to still reposition or remove the stent. Once the stent is fully deployed, i.e. radially expanded, the sheath cannot reconstrain the stent. For example, utilizing a conventional outer sheath/inner catheter delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded into the body lumen. Additionally, retraction of the outer sheath may not be achieved with controlled movement because the physician is manually retracting the outer sheath which may lead to uneven or inadvertent jerking back of the outer sheath that can lead to improper positioning of the stent.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications, for example to prevent stent migration or to properly open a stricture along the entire length of the stricture. An additional drawback occurs with the sheathed stent delivery system where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catchers and hysterics in the movement of the stent. The sheathed stent delivery device also requires more space within an endoscope compared to a sheathless device and also adds additional expense to the delivery system.

Accordingly, in view of the drawbacks of current technology, there is a desire for a delivery system that can increase the control, accuracy and ease of placement of a stent during deployment of the stent within a lumen within a patient. The delivery system would ideally reduce the risk of malfunction while providing for a smoother, more accurate and quicker deployment of the entire stent. The delivery system also would provide the ability to recollapse, recapture, reposition and/or remove the stent after expansion of the stent.

BRIEF SUMMARY

In one aspect, a stent delivery system is provided. The stent delivery system includes an inner elongate shaft including a proximal portion, a distal portion and a lumen extending at least partially therethrough and an outer elongate shaft including a proximal portion, a distal portion and a lumen extending at least partially therethrough, the inner elongate shaft coaxially extending at least partially within the lumen of the outer elongate shaft where the inner and outer elongate shafts movably positionable relative to each other. The stent delivery system also includes a stent positionable on the inner elongate shaft, the stent having a collapsed configuration and an expanded configuration, and having a plurality of openings and a restraining wire having a proximal portion and a distal portion where the proximal portion is operably connected to one of the inner and the outer elongate shaft and the distal portion is operably connected to the other of the inner and the outer elongate shaft and the restraining wire extending at least partially through at least two of the plurality of openings. Movement of the inner and outer elongate shafts relative to each other in a first direction applies tension to at least a portion of the restraining wire to move the stent to the collapsed configuration.

In another aspect, a stent delivery system is provided. The stent delivery system includes an inner elongate shaft having a proximal portion, a distal portion and a lumen extending at least partially therethrough and an outer elongate shaft having a proximal portion, a distal portion and a lumen extending at least partially therethrough. The inner elongate shaft coaxially extends at least partially within the lumen of the outer elongate shaft and the inner and outer elongate shafts are movably positionable relative to each other. A stent is positionable on the inner elongate shaft, the stent having a collapsed configuration and an expanded configuration, the stent having a plurality of openings. The delivery system also includes a restraining wire having a proximal portion and a distal portion, the proximal portion is operably connected to the outer elongate shaft and the distal portion is operably connected to the inner elongate shaft and the restraining wire extends at least partially through at least two of the plurality of openings. Proximal movement of the outer elongate shaft relative to the inner elongate shaft in a first direction applies tension to at least a portion of the restraining wire to move the stent to the collapsed configuration.

In another aspect, a method of delivering a stent is provided. The method includes inserting a distal portion of a stent delivery system into the lumen of a patient. The stent delivery system includes an inner elongate shaft including a proximal portion, a distal portion and a lumen extending at least partially therethrough and an outer elongate shaft including a proximal portion, a distal portion and a lumen extending at least partially therethrough. The inner elongate shaft coaxially extends at least partially within the lumen of the outer elongate shaft and the inner and outer elongate shafts are movably positionable relative to each other. A stent is positionable on the inner elongate shaft, the stent having a collapsed configuration and an expanded configuration and having a plurality of openings. The delivery system also includes a restraining wire having a proximal portion and a distal portion, the proximal portion is operably connected to one of the inner and the outer elongate shaft and the distal portion operably is connected to the other of the inner and the outer elongate shaft and the restraining wire extends at least partially through at least two of the plurality of openings. The method further includes holding the stent in the collapsed configuration with tension applied to at least a portion of the restraining wire for delivery of the stent to the implant site, positioning the stent at the implant site and expanding the stent to the expanded configuration by moving the inner and outer shafts relative to each other to a second position and releasing tension on the restraining wire so the stent moves to the expanded configuration.

DETAILED DESCRIPTION

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly.

As used in the specification, the terms proximal and distal should be understood as being in the terms of a physician using the delivery system. Hence the term distal means the portion of the delivery system which is farthest from the physician and the term proximal means the portion of the delivery system which is nearest to the physician.

Figure 1:
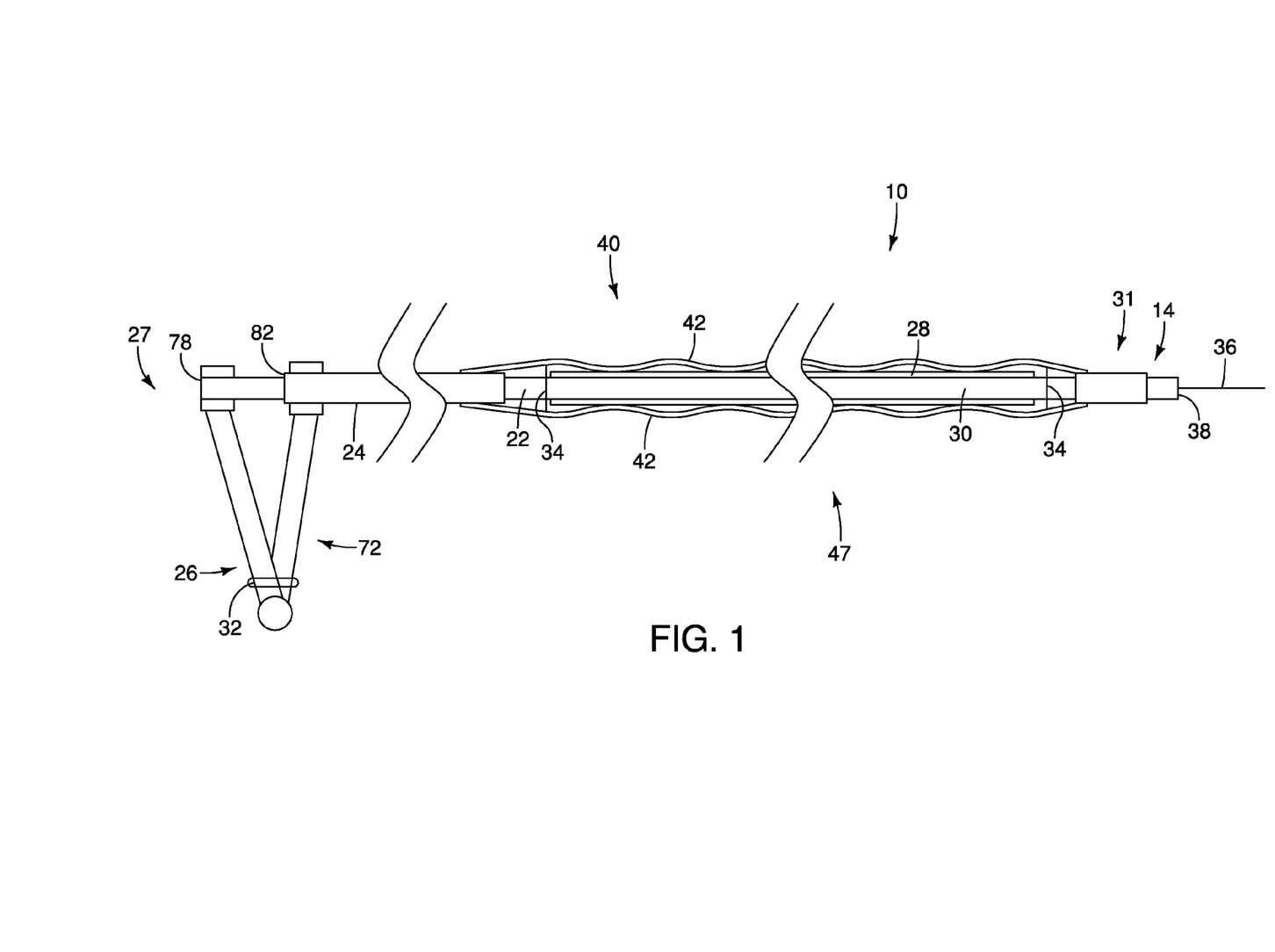
FIG. 1 is a side view of a stent delivery system according to an embodiment of the present invention illustrating a stent in a collapsed configuration.

FIG. 1 illustrates a stent delivery system 10 in accordance with embodiments of the present invention. The stent delivery system 10 includes an inner shaft 22, an outer shaft 24 and a handle 26 at a proximal portion 27 of the system 10. A stent 28 is positionable on a portion 30 of the inner shaft 22 at a distal end portion 31 of the delivery system 10. One or more radiopaque markers 34 may be included on the delivery system 10 to indicate the position of the stent 28. The stent delivery system 10 may also include a guidewire 36 extendable through a port 38 of the inner shaft 22 through a distal tip 41 at the distal end portion 31 of the delivery system 10. As shown in FIG. 1, the stent 28 is in a collapsed configuration 40 positioned against the inner shaft 22.

The stent delivery system 10 may also include a restraining wire 42 that may be extended through a portion of the stent 28 to hold the stent 28 to the delivery device 10. In some embodiments, a plurality of 2 or more restraining wires 42 may be included and extended through a portion of the stent 28. Each restraining wire 42 includes a first portion 44 operably connected to the outer shaft 24. Each restraining wire 42 also includes a second portion 46 operably connected to the inner shaft 22. When a plurality of restraining wires 42 are included to hold the stent 28 to the delivery device 10, the restraining wires 42 may be spaced radially around the stent 28 and spaced apart by uniform distances in some embodiments. For example, if two restraining wires 42 are included, the wires 42 may be spaced apart by 180°, three wires 42 may be spaced apart by 120° and four wires 42 may be spaced apart by 90°, etc. In some embodiments, the restraining wires 42 may be positioned around the stent 28 and spaced apart by unequal distances. The restraining wires 42 may be used to collapse the stent 28 without pulling ends of the stent 28 to collapse the stent 28 due to tension on the stent 28 itself. The restraining wires 42 may be any kind of filament that is suitable for holding the stent 28 in the collapsed configuration 40 and for releasing the stent 28.

The stent delivery system 10 is shown in a first position 47 in FIG. 1 with the inner and outer shafts 22, 24 positioned relative to each other such that each restraining wire 42 is substantially taut to hold the stent 28 against the inner shaft 22 in the collapsed configuration 40. In some embodiments, the second portions 46 of the wires 42 may be connected to the inner shaft 22 with a distal releasable locking member 48. In some embodiments, the first portions 44 of the wires 42 may be connected to the outer shaft 24 with a proximal releasable locking member 50. In some embodiments, the second portions 46 of the wires 42 may be connected to the inner shaft 22 with the distal releasable locking member 48 and the first portions 44 of the wires 42 may be connected to the outer shaft 24 with the proximal releasable locking member 50. In yet other embodiments, one of the first portion 44 or the second portion 46 of the restraining wire 42 may be non-releaseably connected to the outer shaft 24 or the inner shaft 22, respectively. Release of the restraining wire 42 from the stent 28 is described below in more detail.

Figure 5A:
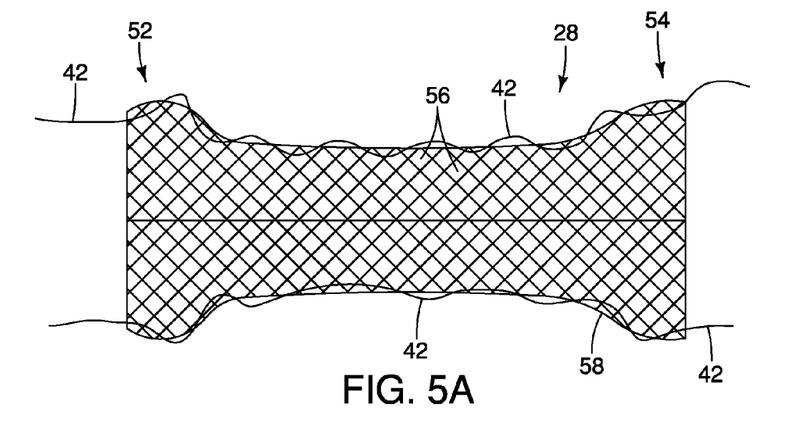
FIGS. 5A-5C illustrate side views of a stent according to embodiments of the present invention.
Figure 5B:
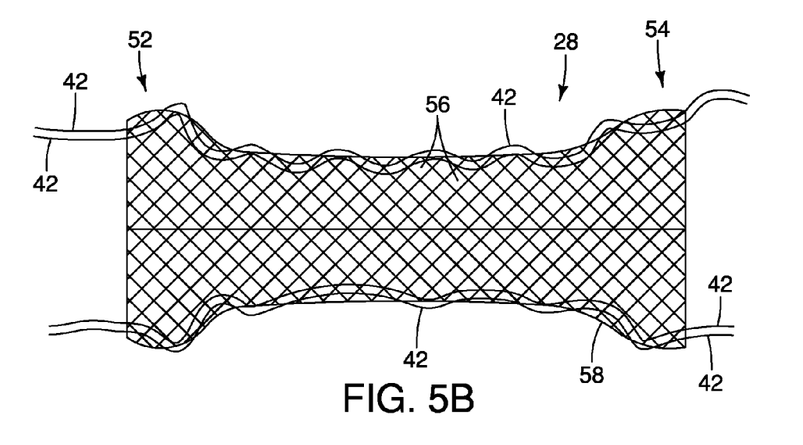
Figure 5C:
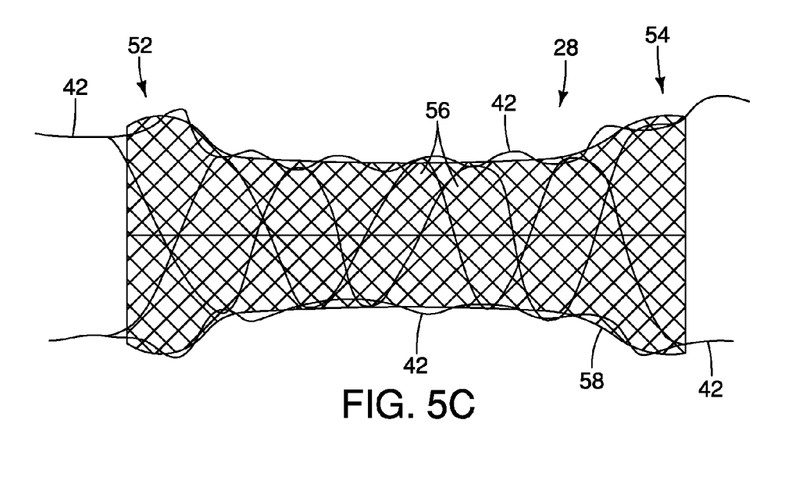

In some embodiments, the stent 28 may be a self-expanding stent. By way of non-limiting example, the stent 28 may be formed as a woven mesh formed from a metal or polymer or a laser cut pattern formed in a metal stent. The stent may also be formed from a bioabsorbable material. One example of a woven stent is the EVOLUTION® stent (Wilson-Cook Medical, Inc.). An exemplary stent 28 is shown in FIGS. 5A-5C and illustrates different non-limiting configurations that may be used for the wire(s) 42. The stent 28 includes a proximal end portion 52 and a distal end portion 54. The stent 28 includes a plurality of openings 56 formed in a stent wall 58. Each wire 42 may be threaded through a plurality of openings 56 as shown in FIG. 5A where the wire 42 extends generally along the longitudinal axis of the stent 28. One or more wires 42 may extend through the plurality of openings 56. In some embodiments, two wires 42 may extend through the plurality of openings 56 in the stent 28 and be positioned adjacent to each other as shown in FIG. 5B. In some embodiments, additional pairs of wires 42 may also extend through the stent. As shown in FIG. 5C, one or more wires 42 may extend helically through the plurality of openings 56 in the stent 28. In some embodiments, a plurality of wires 42 may extend helically through the stent 28. The number of openings 56 through which the wire 42 extends will depend on a number of conditions, including but not limited to the length of the stent, the diameter of the stent, the material of the stent, the force on the wire that is required to collapse the stent against the inner shaft and the like.

Figure 2:
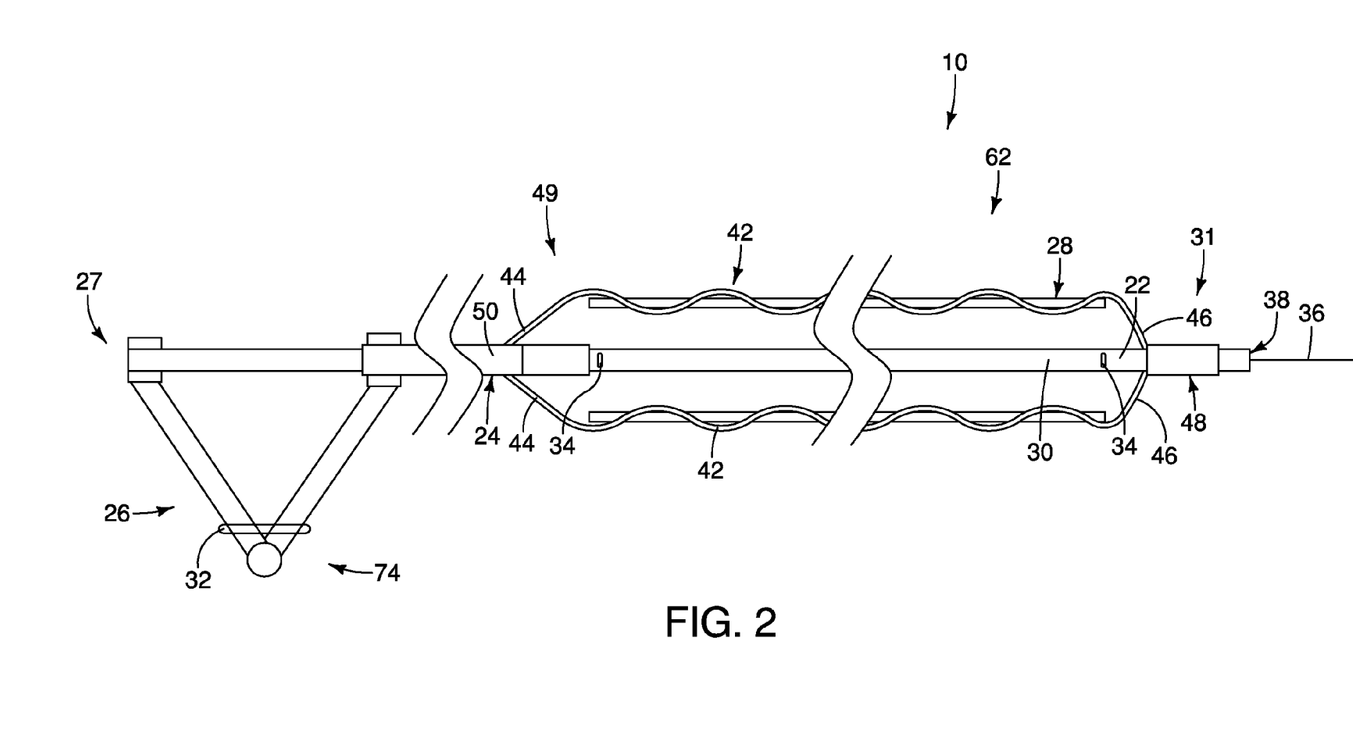
FIG. 2 is a side view of the stent delivery system shown in FIG. 1 illustrating the stent in an expanded configuration.

FIG. 2 illustrates the stent delivery system 10 with the stent 28 in an expanded configuration 62 where the stent 28 is expanded away from the inner shaft 22. The stent delivery system 10 is shown in a second position 49 with the inner and outer shafts 22, 24 positioned relative to each other such that tension on each wire 42 is released so the stent 28 expands to the expanded configuration 62. In some embodiments, the inner and outer shafts 22, 24 may be coaxially positioned and longitudinally movable relative to each other to facilitate the placement of the stent 28. As shown in FIG. 1, the inner shaft 22 is moved distally and the outer shaft 24 is moved proximally so that tension is placed on the restraining wire 42 to position the stent 28 in the collapsed configuration 40. The handle 26 is shown in a first position 72. As shown in FIG. 2, the inner shaft 22 is moved proximally and the outer shaft 24 is moved distally relative to the position shown in FIG. 1 to release the tension of the restraining wire 42 and expand the stent 28 from the collapsed configuration 40 to the expanded configuration 62. The handle 26 is shown in a second position 74 in FIG. 2. The relative movement of the stent delivery system 10 illustrated in FIGS. 1 and 2 is shown by way of example and meant to be non-limiting. Other configurations for the arrangement of the connection of the stent to the inner and outer shafts for moving the stent between the collapsed and expanded configurations are also possible. In some embodiments, one of the inner shaft 22 and the outer shaft 24 may be moved relative to the other of the inner shaft 22 and the outer shaft 24 to move the stent 28 between the collapsed configuration 40 and the expanded configuration 62. The handle 26 may include a lock 32 to releasably lock the handle 26 in the first position 72 or the second position 74. In some embodiments, the lock 32 may be positionable so that the relative position of the inner and outer shafts 22, 24 may be releasably locked in any longitudinal position.

As shown in FIG. 2, each wire 42 is threaded through a portion of the stent 28 and remains operably connected to the inner shaft 22 and the outer shaft 24 with the stent in the expanded configuration 62. The connection allows the stent 28 to be moved between the collapsed configuration 40 and the expanded configuration 62 and back to the collapsed configuration 40, for example for repositioning the stent 28 within a patient's lumen. The stent 28 may be moved between the collapsed and expanded configurations 40, 62 any number of times until the stent 28 is released from connection to the inner and outer shafts 22, 24 as described in more detail below.

Figure 3:
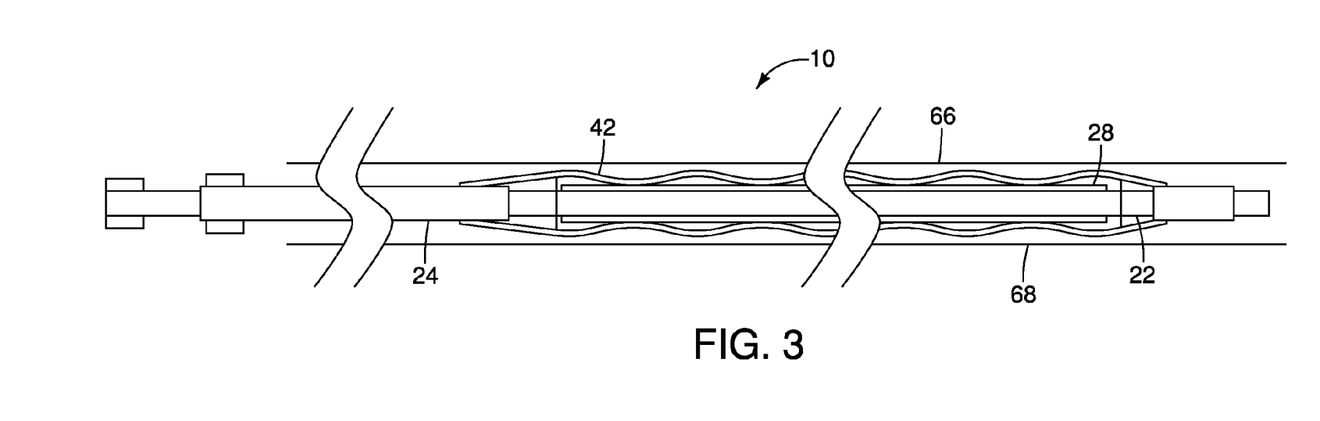
FIG. 3 is a side view of an embodiment of the stent delivery system according to an embodiment of the present invention.

The stent delivery system 10 may optionally include an outer sheath 66 slidably positionable over a portion of the outer shaft 24 and the inner shaft 22 to cover the stent 28 as shown in FIG. 3. The optional outer sheath 66 is shown extended distally over the stent 28 forming a smooth outer surface 68 of the delivery system 10. The outer sheath 66 may be provided to facilitate a smoother delivery of the stent 28 to the desired location and is not required for collapsing the stent 28 in the collapsed configuration 40. When present, the outer sheath 66 may provide some compressive force to the stent 28 in addition to the wires 42. The outer sheath 66 may be operably connected to the handle 26 to provide longitudinal movement of the outer sheath 66 to expose the stent 28. The outer sheath 66 may be withdrawn proximally.

Figure 4:
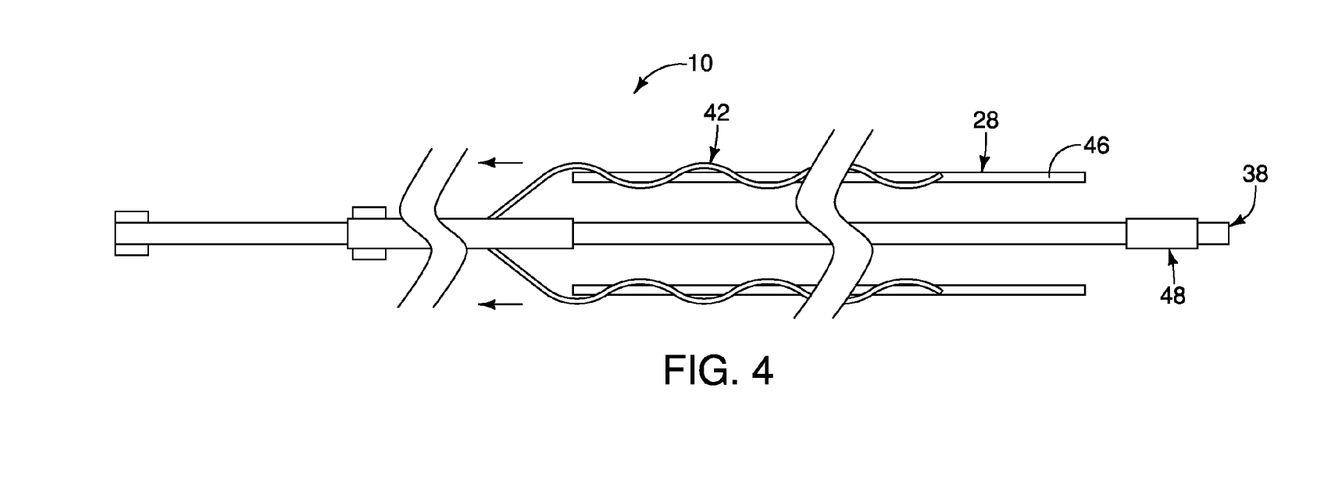
FIG. 4 is a side view of the stent delivery shown in FIG. 2.
Figure 6:
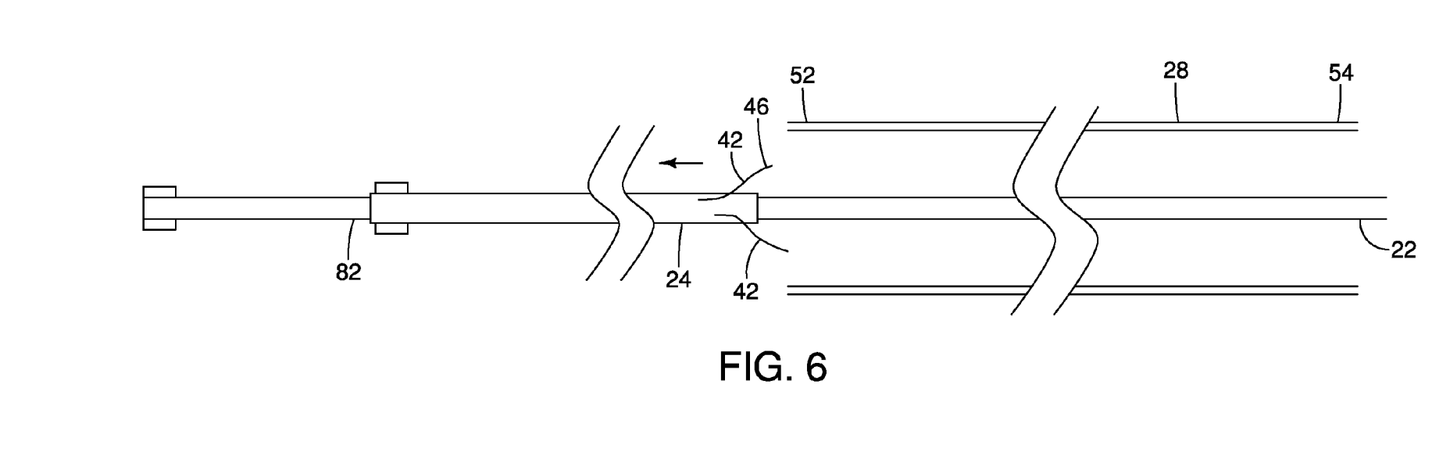
FIG. 6 is a side view of the stent delivery system according to an embodiment of the present invention with the restraining wire withdrawn from the stent.
Figure 7:
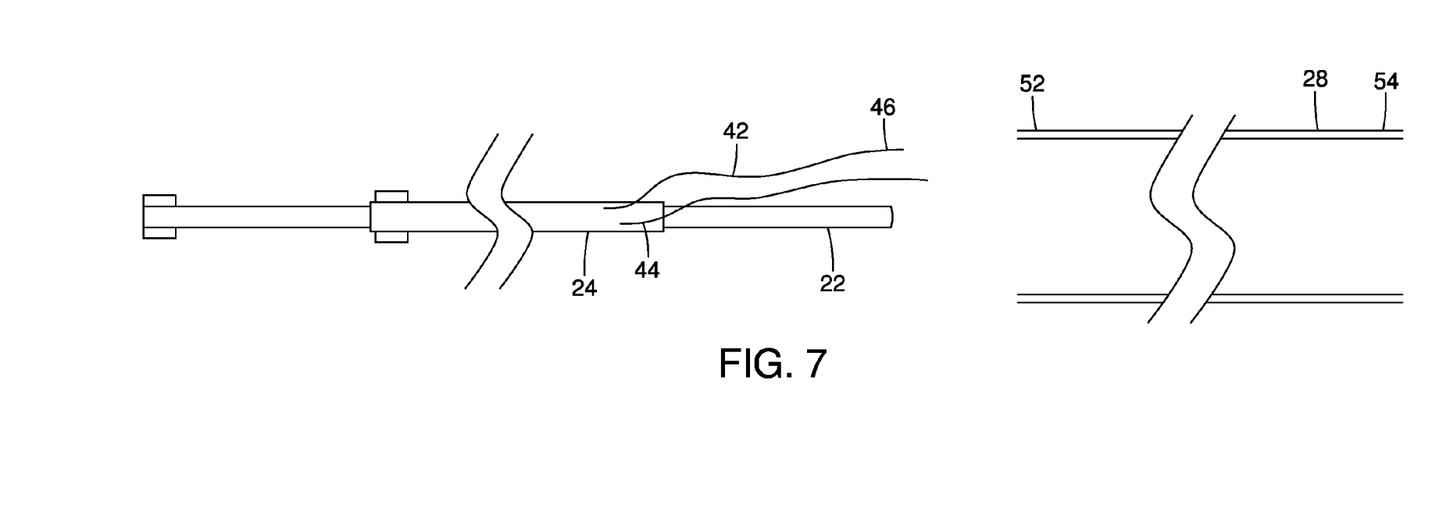
FIG. 7 is a side view of the stent delivery system according to an embodiment of the present invention with the restraining wire withdrawn from the stent.

Once the stent 28 is positioned at a delivery site in a patient's lumen, the delivery system 10 may be withdrawn. In some embodiments, the restraining wires 42 are withdrawn from the stent 28 and removed from the patient with the inner and outer shafts 22, 24. In some embodiments, the restraining wires 42 remain with the stent 28 and the inner and outer shafts 22, 24 are withdrawn from the patient. FIG. 4 illustrates an embodiment of the delivery system 10 with the wires 42 being proximally withdrawn to release the stent 28 from the delivery system 10. The stent 28 is in the expanded configuration 62 and representative of the stent being properly positioned in the patient's lumen. As shown, the second portion 46 of the wire 42 is released from the distal releasable locking member 48 and is withdrawn through the openings 56 in the stent 28 and out of the proximal end 52 of the stent 28. FIG. 6 illustrates the wire 42 completely withdrawn from the stent 28. Once the wire 42 is completely withdrawn with the stent 28 released in position within the patient's lumen, the inner shaft 22 may be proximally withdrawn from the stent 28 and the delivery system 10 removed. The wire 42 may be proximally withdrawn by pulling the wire 42 through a lumen 82 of the outer shaft 24 as shown in FIG. 6. In some embodiments, the restraining wire 42 may be non-releasably connected to the outer shaft 24 at the first portion 44 of the restraining wire 42 so that the restraining wire 42 is proximally withdrawn from proximal end 52 of the stent 28 by proximally withdrawing the stent delivery system 10 from the delivery site within the patient's lumen with the stent 28 remaining at the delivery site as shown in FIG. 7.

Figure 8:
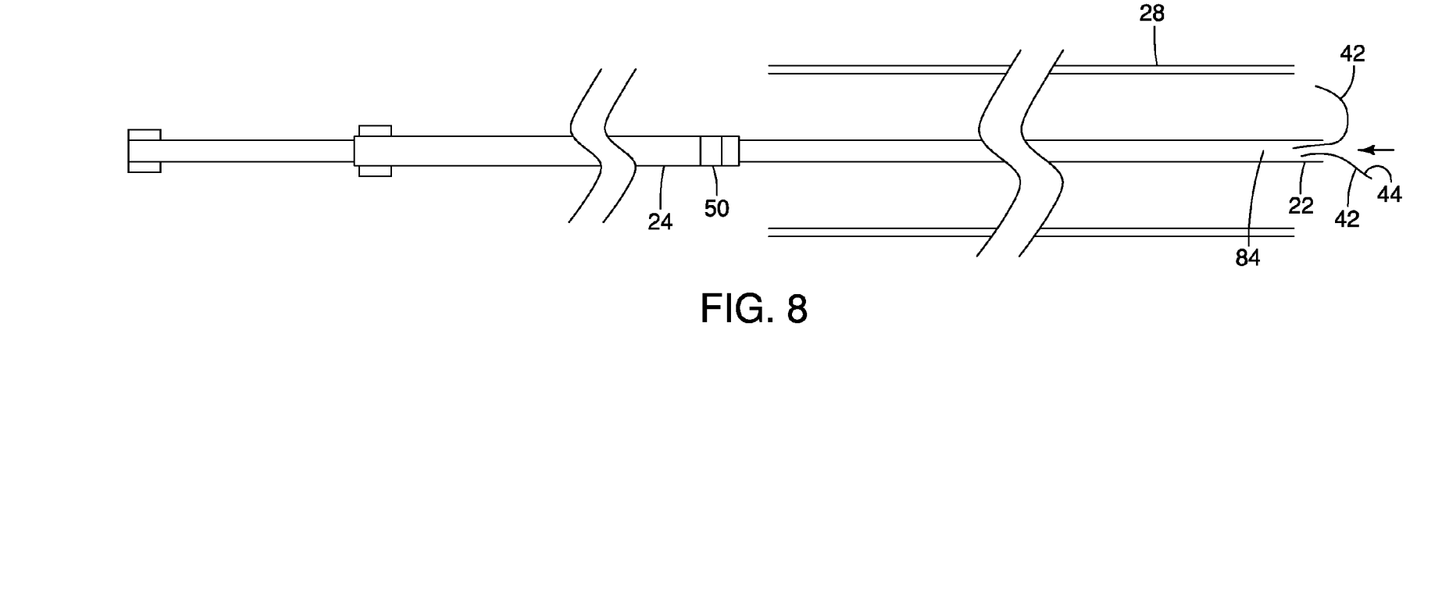
FIG. 8 is a side view of the stent delivery system according to an embodiment of the present invention with the restraining wire withdrawn from the stent.

In some embodiments, the restraining wires 42 may be releasable from the proximal restraining member 50 and may be withdrawn by pulling the second portion 46 of the wire 42 through a lumen 84 of the inner shaft 22 so that the wire 42 is pulled proximally once the wire 42 is within the lumen 84. The first portion 44 of the wire 42 is completely withdrawn from the distal end 54 of the stent 28 by proximally pulling the second portion 46 so that the first portion 44 of the wire 42 moves distally through the stent 28 as shown in FIG. 8 to remove the wire 42. The stent delivery system 10 may be proximally withdrawn from the lumen of the patient, leaving the stent 28 at the delivery site. In some embodiments, the second portion 46 of the restraining wire 42 may be non-releasably connected to the inner shaft 22. The restraining wire 42 in this embodiment may be withdrawn from the stent 28 by distally advancing the inner shaft 22 relative to the stent 28 until the wire 42 is completely distally withdrawn from the distal end 54 of the stent 28 and then proximally withdrawing the delivery system 10 from the patient's lumen (not shown).

Figure 9:
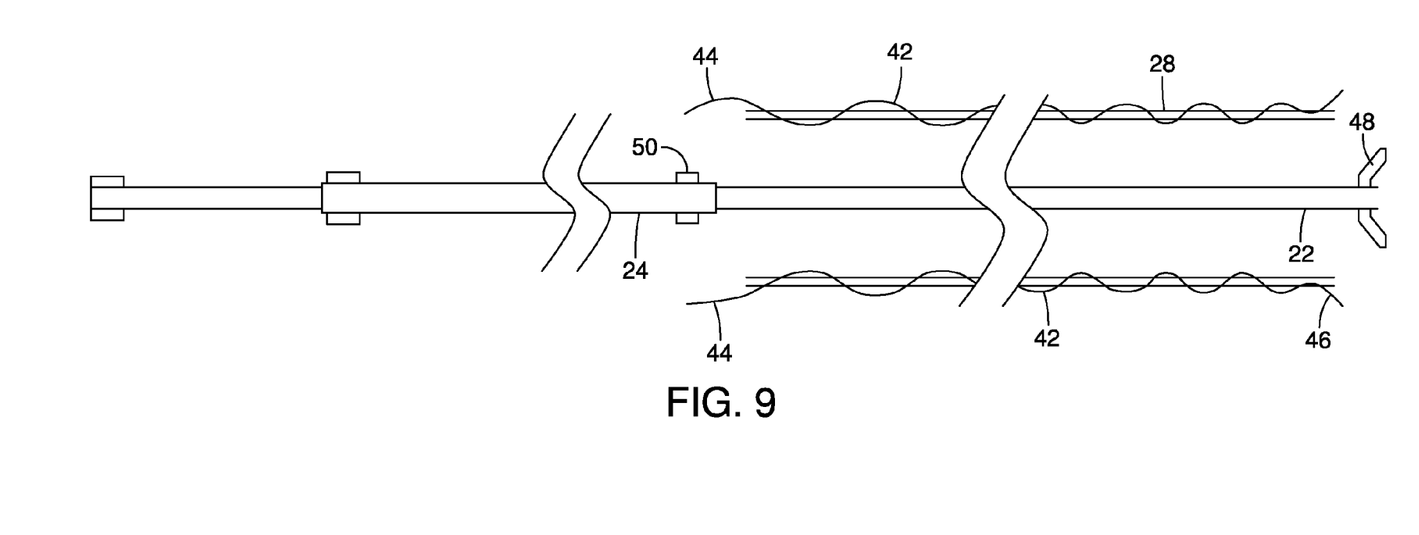
FIG. 9 is a side view of the stent delivery system according to an embodiment of the present invention with the restraining wire released from the delivery system.

In some embodiments, the restraining wires 42 may remain with the stent 28 as shown in FIG. 9. The first and second portions 44, 46 of the wires 42 may be released from the proximal and distal releasable locking members 50, 48, respectively. The inner shaft 22 may be withdrawn from the stent 28 and the delivery system 10 removed from the patient's lumen. In some embodiments, the restraining wires 42 that remain with the stent 28 may be biodegradable.

Figure 10:
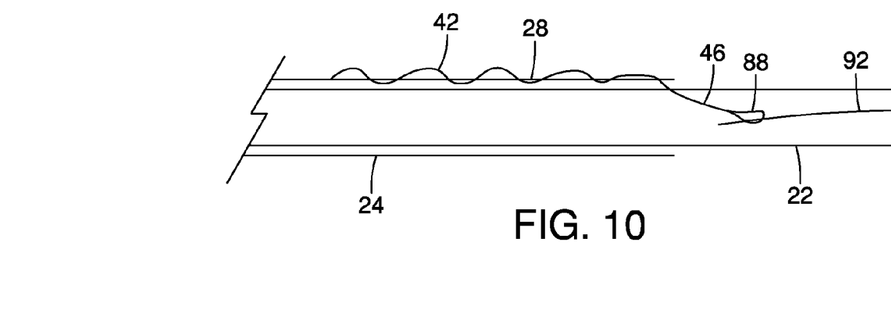
FIG. 10 is a partial side view of a releasable locking member of the stent delivery system according to an embodiment of the present invention.

The releasable locking members 48 and 50 may be any type of mechanism that can releaseably hold the first and second portions 44, 46 of the wires 42 for delivery, positioning and repositioning of the stent 28. By way of non-limiting example, the releasable locking members 48, 50 may be releasable bands secured around the inner and outer shafts, hooks, adhesives, wires, and the like. For example, the wire 42 may include a loop 88 on the distal portion 46 of the wire 42. The loop 88 may be releasably secured to the inner shaft 22 with a wire 92 that is positioned through the loop 88 to hold the wire 42 to the inner shaft 22 as shown in FIG. 10. The wire 92 may be withdrawn from the loop 88, for example by proximally withdrawing the wire 92 through the lumen 84 of the inner shaft 22. The proximal portion 44 of the wire 42 may be held by similar or different mechanisms as the distal portion 46 of the wire 42. Other mechanisms may also be used for releasably holding the wire 42 to the inner and/or outer shafts 22, 24.

The materials used to manufacture the components of the stent delivery systems described herein may be any materials known to one skilled in the art that are suitable for use in patients. By way of non-limiting example, the shafts and sheath may be formed from polytetrafluoroethylene (PTFE) particularly when a low friction outer sheath is desirable. Nylon and HDPE may also be used for clarity. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon including multi-layer or single layer structures and the like and may also include reinforcement wires, braid wires, coils, coil springs and or filaments.

The stent may be formed but is not limited to the following materials: Nickel titanium alloys, for example, nitinol, stainless steel, cobalt alloys and titanium alloys. The wires may be made from a metallic alloy such as stainless steel or nickel titanium. In some embodiments, the wires may be made from polymers having sufficient strength to hold the stent in the collapsed configuration. The wires may be single, multiple, braided or twisted. In some embodiments, the wires or segments thereof may be coated, for example with a coating such as PTFE to aid in removal of the wires from the stent 28. In some embodiments, the stent and/or the wires may be made from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyanates; polyphosphazines; polyethers including polyglycols, polyorthoesters; epoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen.

Other suitable biocompatible materials may also be used for any of the components described herein.

Operation of the stent delivery systems of the present invention is described with reference to the stent delivery system 10 by way of non-limiting example. Alternative methods of operating the system may also be used. The stent delivery system 10 may be provided in a sterile packaging. The stent 28 may be provided in the expanded configuration 62 or constrained configuration 40 within the packaging. For example, some stent materials may weaken or otherwise deform when stored in a collapsed configuration 40 during shipping and storage. The stent 28 may be provided in the expanded configuration 62 and be moved to the collapsed configuration 40 by operation of the handle 26 to the first position 72 shown in FIG. 1 prior to delivery to the patient.

The delivery system 10 may be delivered to the patient using an endoscope that may be positioned within the lumen so the operator can view a proximal side of a stricture to be treated with the stent 28. The guidewire 36 is inserted through the stricture. The proper length stent 28 is selected based on the stricture measurement. The operator inserts the distal portion 31 of the stent delivery system into the patient's lumen with the stent 28 in the collapsed configuration 40 on the inner shaft 22. The guidewire 36 may be inserted first to navigate a tortuous pathway to the treatment site and the system 10 is delivered through the working channel of the endoscope over the guidewire 36 to the treatment site. Alternatively, the stent delivery system 10 may be inserted into the patient's lumen without the use of an endoscope, depending on the size and location of the lumen.

The collapsed stent 28 may be moved within the lumen to correctly position the stent 28 at the treatment site. The stent 28 is moved to the expanded configuration 66 by movement of the inner shaft 22 relative to the outer shaft 24 to release the tension on the wire 42, for example by moving the outer shaft 24 distally and/or the inner shaft 22 proximally. The position of the expanded stent 28 can be monitored. If necessary, The stent 28 may be returned to the collapsed configuration 40 by the operator moving the inner shaft distally and or the outer shaft proximally to return the tension to the wire 42 and collapse the stent 28 onto the inner shaft 22, for example if the stent 28 is incorrectly positioned. The stent 28 may be moved from the collapsed configuration 40 to the expanded configuration 62 as many times as needed.

Once the proper position for the stent 28 is achieved within the patient's lumen, the proximal and or distal releasable locking member 50, 48 may be released to release the wire 42. The delivery system 10 is withdrawn proximally from the patient.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A stent delivery system comprising:
an inner elongate shaft including a proximal portion, a distal portion and a lumen extending at least partially therethrough;

an outer elongate shaft including a proximal portion, a distal portion and a lumen extending at least partially therethrough, the inner elongate shaft coaxially extending at least partially within the lumen of the outer elongate shaft, the inner and outer elongate shafts movably positionable relative to each other;

a stent positionable on the inner elongate shaft, the stent having a collapsed configuration and an expanded configuration, the stent having a plurality of openings;

a restraining wire having a proximal portion and a distal portion, the proximal portion operably connected to one of the inner and the outer elongate shaft and the distal portion operably connected to the other of the inner and the outer elongate shaft, the restraining wire extending at least partially through at least two of the plurality of openings;

wherein movement of the inner and outer elongate shafts relative to each other in a first direction applies tension to at least a portion of the restraining wire to move the stent to the collapsed configuration.

2. The stent delivery system of claim 1, wherein movement of the inner and outer elongate shafts relative to each other in a second direction releases the tension on the at least a portion of the restraining wire.

3. The stent delivery system of claim 1, further comprising a plurality of restraining wires, each restraining wire having a proximal portion and a distal portion, the proximal portion operably connected to one of the inner and the outer elongate shaft and the distal portion operably connected to the other of the inner and the outer elongate shaft, each of the plurality of restraining wires extending at least partially through at least two of the plurality of openings.

4. The stent delivery system of claim 3, wherein the plurality of restraining wires are equally spaced apart around a circumference of the stent.

5. The stent delivery system of claim 1, wherein the restraining wire is completely removable from connection with the stent to release the stent from the delivery system.

6. The stent delivery system of claim 1, wherein the stent is repeatedly movable between the constrained configuration and the expanded configuration.

7. The stent delivery system of claim 1, wherein the restraining wire is proximally removable from the stent.

8. The stent delivery system of claim 1, wherein the restraining wire is distally removable from the stent.

9. The stent delivery system of claim 1, wherein the proximal and distal portions of the restraining wire are removable from the inner and the outer shaft.

10. The stent delivery system of claim 1, wherein the system further comprises a handle movable from a first position to a second position to change a longitudinal position of the inner shaft relative to the outer shaft.

11. A stent delivery system comprising:

an inner elongate shaft including a proximal portion, a distal portion and a lumen extending at least partially therethrough;

an outer elongate shaft including a proximal portion, a distal portion and a lumen extending at least partially therethrough, the inner elongate shaft coaxially extending at least partially within the lumen of the outer elongate shaft, the inner and outer elongate shafts movably positionable relative to each other;

a stent positionable on the inner elongate shaft, the stent having a collapsed configuration and an expanded configuration, the stent having a plurality of openings;

a restraining wire having a proximal portion and a distal portion, the proximal portion operably connected to the outer elongate shaft and the distal portion operably connected to the inner elongate shaft, the restraining wire extending at least partially through at least two of the plurality of openings;

wherein proximal movement of the outer elongate shaft relative to the inner elongate shaft in a first direction applies tension to at least a portion of the restraining wire to move the stent to the collapsed configuration.

12. The stent delivery system of claim 11, wherein the distal portion of the restraining wire is removably connected to the inner shaft.

13. The stent delivery system of claim 11, wherein the system further comprises a distal releasable locking member releasably locking the distal portion of the restraining wire to the inner elongate shaft.

14. The stent delivery system of claim 11, wherein the system further comprises a proximal releasable locking member releasably locking the proximal portion of the restraining wire to the outer elongate shaft.

15. The stent delivery system of claim 11, wherein the restraining wire is proximally removable from the stent to completely release the stent.

16. The stent delivery system of claim 11, wherein the proximal portion of the restraining wire is non-removably connected to the outer shaft.

* * * * *